United States Patent
Thirumalai Rajan et al.

(10) Patent No.: US 10,633,390 B2
(45) Date of Patent: Apr. 28, 2020

(54) PROCESS FOR THE PREPARATION OF [(1S,2R)-3-[[(4-AMINOPHENYL)SULFONYL] (2-METHYLPROPYL)AMINO]-2-HYDROXY-1-(PHENYLMETHYL)PROPYL]-CARBAMIC ACID (3R,3AS,6AR)HEXAHYDRO FURO [2,3-B]FURAN-3-YL ESTER AND ITS AMORPHOUS FORM

(71) Applicant: MSN LABORATORIES PRIVATE LIMITED, Hyderabad, Telangana (IN)

(72) Inventors: Srinivasan Thirumalai Rajan, Telangana (IN); Sajja Eswaraiah, Telangana (IN); Revu Satyanarayana, Telangana (IN)

(73) Assignee: MSN LABORATORIES PRIVATE LIMITED, Medak, Hyderabad, Telangana (IN)

( * ) Notice: Subject to any disclaimer, the term of this patent is extended or adjusted under 35 U.S.C. 154(b) by 0 days.

(21) Appl. No.: 15/739,948

(22) PCT Filed: Jun. 27, 2016

(86) PCT No.: PCT/IN2016/000168
§ 371 (c)(1),
(2) Date: Dec. 26, 2017

(87) PCT Pub. No.: WO2016/207907
PCT Pub. Date: Dec. 29, 2016

(65) Prior Publication Data
US 2018/0370982 A1  Dec. 27, 2018

(30) Foreign Application Priority Data
Jun. 25, 2015  (IN) ............................ 3197/CHE/2015

(51) Int. Cl.
*C07D 493/04* (2006.01)

(52) U.S. Cl.
CPC .................................. *C07D 493/04* (2013.01)

(58) Field of Classification Search
CPC .................................................... C07D 493/04
See application file for complete search history.

(56) References Cited

FOREIGN PATENT DOCUMENTS

| CN | 104230877 | 12/2014 |
|----|-----------|---------|
| WO | WO 2008/112286 | 9/2008 |

OTHER PUBLICATIONS

International Search Report issued in International patent application No. PCT/IN2016/000168, dated Oct. 17, 2016.

*Primary Examiner* — Timothy R Rozof
(74) *Attorney, Agent, or Firm* — IP Pundit LLC

(57) ABSTRACT

The present invention relates to an improved process for the preparation of [(1S,2R)-3-[[(4-aminophenyl)sulfonyl] (2-methylpropyl)amino]-2-hydroxy-1-(phenylmethyl)propyl]-carbamic acid (3R,3aS,6aR)hexahydrofuro[2,3-b]furan-3-yl ester compound of formula-1 represented by the following structural formula:

Formula-1

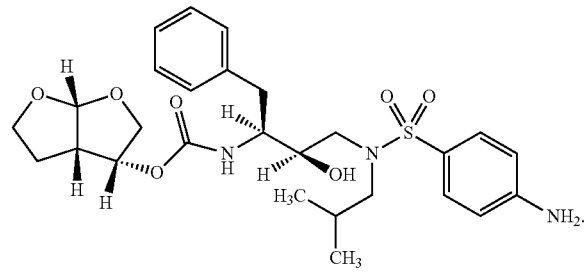

18 Claims, 2 Drawing Sheets

PROCESS FOR THE PREPARATION OF [(1S,2R)-3-[[(4-AMINOPHENYL)SULFONYL] (2-METHYLPROPYL)AMINO]-2-HYDROXY-1-(PHENYLMETHYL)PROPYL]-CARBAMIC ACID (3R,3AS,6AR)HEXAHYDRO FURO [2,3-B]FURAN-3-YL ESTER AND ITS AMORPHOUS FORM

RELATED APPLICATIONS

This application claims the benefit of priority of our Indian patent application number 3197/CHE/2015 filed on 25 Jun. 2015 which is incorporated herein by reference.

FIELD OF THE INVENTION

The present invention relates to an improved process for the preparation of [(1S,2R)-3-[[(4-aminophenyl)sulfonyl](2-methylpropyl)amino]-2-hydroxy-1-(phenylmethyl)propyl]-carbamic acid (3R,3aS,6aR)hexahydrofuro[2,3-b]furan-3-yl ester compound of formula-1 represented by the following structural formula:

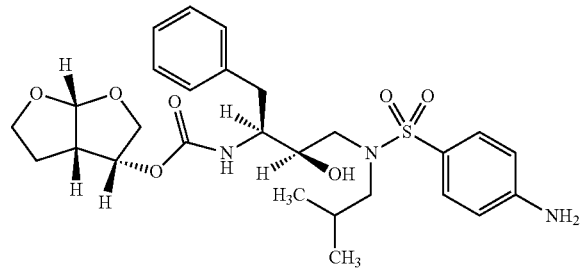

Formula-1

The present invention also provides an improved process for the preparation of (3R,3aS,6aR)-hexahydrofuro[2,3-b]furan-3-ol compound of formula-2,

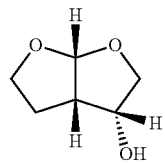

Formula-2 which is a key intermediate and is useful in the preparation of compound of formula-1.

BACKGROUND OF THE INVENTION

[(1S,2R)-3-[[(4-aminophenyl)sulfonyl](2-methylpropyl)amino]-2-hydroxy-1-(phenyl methyl)propyl]-carbamic acid (3R,3aS,6aR)hexahydrofuro[2,3-b]furan-3-yl ester is commonly known as Darunavir. The Darunavir is a protease inhibitor drug used to treat HIV infection. Prezista is an OARAC recommended treatment option for treatment-naïve and treatment-experienced adults and adolescents.

Darunavir was first generically disclosed in U.S. Pat. No. 5,843,946 and specifically disclosed in U.S. Pat. No. 6,248,775.

U.S. Pat. No. 7,126,015 discloses process for the preparation of (3R,3aS,6aR)-hexahydrofuro[2,3-b]furan-3-ol.

The disclosed process involves cyclisation of (R)-3-((R)-2,2-dimethyl-1,3-dioxolan-4-yl)-4-nitrobutan-1-ol in presence of potassium tert-butoxide in isopropanol followed by reaction with concentrated hydrochloric acid to give mixture of compound of formula-2 i,e. (3R,3aS,6aR)-hexahydrofuro[2,3-b]furan-3-ol in a ratio of 78:22 which results in the formation of final product with low yield and low purity. Further the final compound of formula-2 was purified by column chromatography, which is a laborious and time consuming process and also it is not suitable for commercial scale purpose.

Hence, there is a need in the art to develop an improved, economical viable and efficient, simple process for the preparation of (3R,3aS,6aR)-hexahydrofuro[2,3-b]furan-3-ol compound of formula-2 with high yield and purity.

BRIEF DESCRIPTION OF THE INVENTION

The first aspect of the present invention is to provide an improved process for the preparation of (3R,3aS,6aR)-hexahydrofuro[2,3-b]furan-3-ol compound of formula-2.

The second aspect of the present invention is to provide an improved process for the preparation of (R,E)-ethyl-3-(2,2-dimethyl-1,3-dioxolan-4-yl)acrylate compound of formula-8.

The third aspect of the present invention is to provide an improved process for the preparation of (R)-ethyl-3-((R)-2,2-dimethyl-1,3-dioxolan-4-yl)-4-nitrobutanoate compound of formula-9.

The fourth aspect of the present invention is to provide an alternate process for the preparation of (3R,3aS,6aR)-hexahydrofuro[2,3-b]furan-3-ol compound of formula-2.

The fifth aspect of the present invention is to provide a process for the preparation of Amorphous [(1S,2R)-3-[[(4-aminophenyl)sulfonyl](2-methylpropyl)amino]-2-hydroxy-1-(phenylmethyl)propyl]carbamic acid (3R,3aS,6aR)-hexahydrofuro[2,3-b]furan-3-yl ester compound of formula-1.

The sixth aspect of the present invention is to provide a one-pot process for the preparation of (3R,3aS,6aR)-hexahydrofuro[2,3-b]furan-3-ol compound of formula-2.

DETAILED DESCRIPTION OF THE INVENTION

Figure 1:
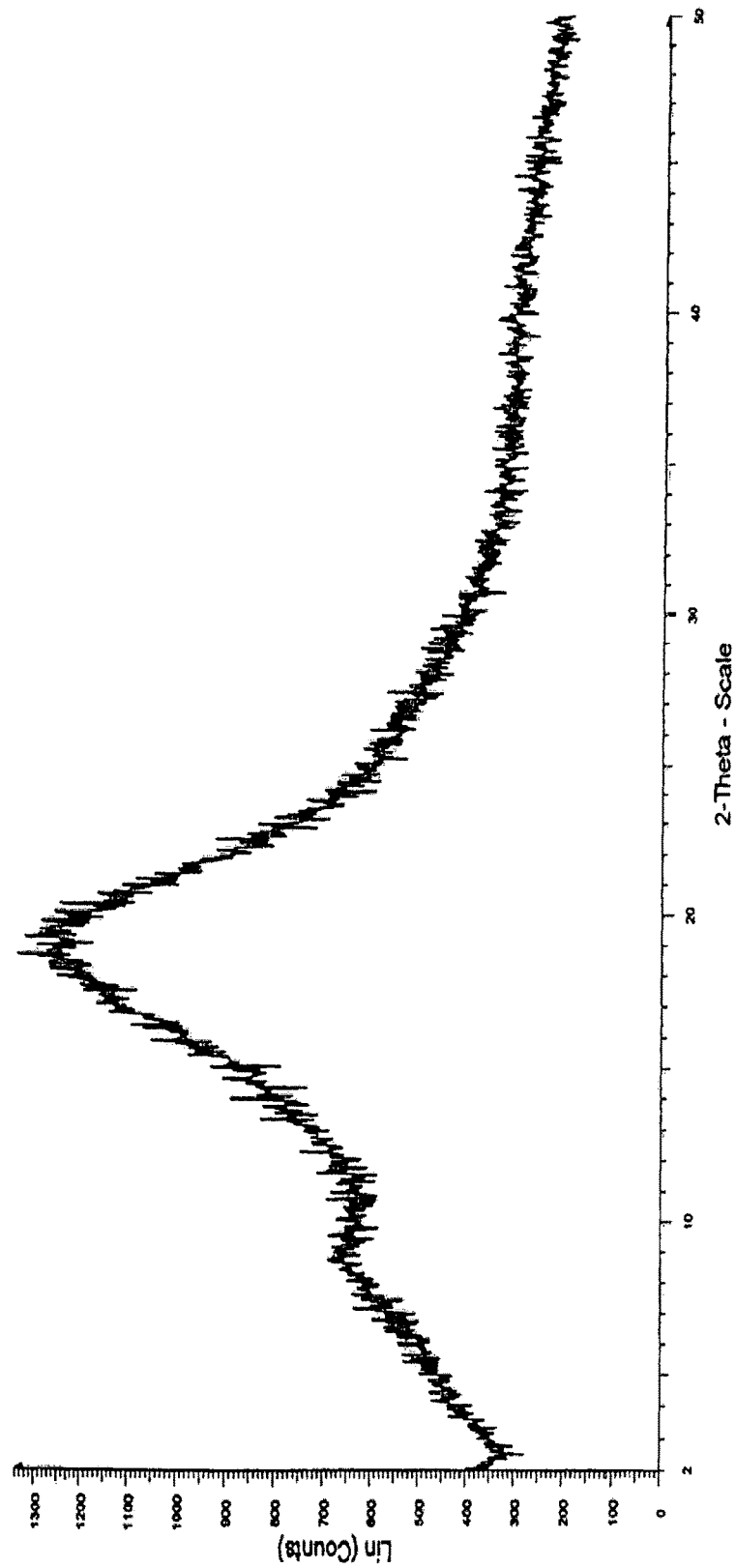
FIG. 1: Illustrates the PXRD pattern of amorphous [(1S,2R)-3-[[(4-aminophenyl) sulfonyl](2-methylpropyl)amino]-2-hydroxy-1-(phenylmethyl)propyl]carbamic acid (3R,3aS,6aR)-hexahydrofuro[2,3-b]furan-3-yl ester compound of formula-1.

The term "suitable solvent" used in the present invention includes, but not limited to "ester solvents" such as ethyl acetate, methyl acetate, isopropyl acetate, n-butyl acetate and the like; "ether solvents" such as tetrahydrofuran, dimethyl ether, diethyl ether, diisopropyl ether, methyl tert-butyl ether, 1,4-dioxane and the like; "hydrocarbon solvents" such as toluene, hexane, heptane, pet ether, benzene, xylene, cyclohexane and the like; "polar aprotic solvents" such as dimethyl acetamide, dimethylsulfoxide, dimethylformamide, N-methyl-2-pyrrolidone and the like; "ketone solvents" such as acetone, methyl ethyl ketone, methyl isobutyl ketone and the like; "alcoholic solvents" such as methanol, ethanol, n-propanol, isopropanol, n-butanol, isobutanol, tert-butanol and the like; "chloro solvents" such as dichloromethane, chloroform, dichloroethane, carbon tetrachloride and the like; "nitrile solvents" such as acetonitrile, butyronitrile, isobutyronitrile and the like; "protic solvent" such as acetic acid; "polar solvent" such as water or mixtures thereof.

The term "base" used herein the present invention until unless specified is selected from inorganic bases like "alkali metal hydroxides" such as lithium hydroxide, sodium hydroxide, potassium hydroxide and the like; "alkali metal carbonates" such as sodium carbonate, potassium carbonate, lithium carbonate, cesium carbonate and the like; "alkali metal bicarbonates" such as sodium bicarbonate, potassium bicarbonate, lithium bicarbonate, cesium bicarbonate and the like; "alkali metal hydrides" such as sodium hydride, potassium hydride, lithium hydride and the like; "alkali metal alkoxides" such as sodium methoxide, sodium ethoxide, sodium tert-butoxide, potassium methoxide, potassium ethoxide, potassium tert-butoxide and the like; ammonia; and organic bases such as triethyl amine, methyl amine, ethyl amine, 1,8-Diazabicyclo[5.4.0]undec-7-ene (DBU), Tetra-n-butylammonium fluoride (TBAF), 1,5-Diazabicyclo (4.3.0)non-5-ene (DBN), lithium dioisoporpylamide (LDA), n-butyl lithium, tribenzylamine, isopropyl amine, diisopropylamine, diisopropylethylamine, N-methylmorpholine, N-ethylmorpholine, piperidine, dimethylaminopyridine, morpholine, pyridine, 2,6-lutidine, 2,4,6-collidine, imidazole, 1-methylimidazole, 1,2,4-triazole, 1,4-diazabicyclo [2.2.2]octane (DABCO) or mixtures thereof.

The "suitable oxidizing agent" used herein the present invention is selected from peroxides such as oxygen, oxygen/Pt, ozone, hydrogen peroxide, hydrogen peroxide/HCl in presence of hydroxyl amine hydrochloride, peroxydisulfuric acid, peroxymono sulfuric acid; nascent oxygen, chlorite, chlorate, perchlorates of alkali and alkaline earth metals such as sodium chlorite, sodium chlorate, sodium hypochlorite, calcium chlorite, sodium chlorite/$H_2O_2$, calcium hypochlorite and the like; oxalyl chloride in combination with dimethyl sulfoxide, trichloroisocyanuric acid in combination with TEMPO, nitric acid, silver nitrate, potassium nitrate, silver oxide, copper (II) oxide, sodium perborate, hypochlorous acid, tollen's reagent (silver nitrate/ammonia), lithium bromide/triethylamine, $Br_2$/sodium acetate/acetic acid; hexavalent chromium compounds such as chromic and dichromic acids and chromium trioxide, chromium trioxide/$H_2SO_4$ pyridinium chlorochromate (PCC), chromyl chloride, chromate/dichromate compounds such as potassium dichromate, sodium dichromate, sodium dichromate optionally in presence of sulfuric acid; permanganate compounds such as potassium permanganate and the like; manganate compounds such as potassium manganate and the like; peracids such as perbenzoic acid, Peroxy acetic acid, m-chloroperbenzoic acid, trifluoro peracetic acid and the like; chromium complexes such as (1,10-phenonthrolin)$H_2CrOCl_5$ (1,10-phenonthrolin) $CrOCl_3$, ($\alpha$, $\alpha$'-bipyridyl) $H_2CrOCl_5$, ($\alpha$, $\alpha$'-bipyridyl) $CrOCl_3$ and other well-known oxidizing agents.

The suitable "reducing agent" is selected from Lithium aluminum hydride (LiAlH4), Nascent (atomic) hydrogen, hydroquinone, sodium amalgum, diborane, sodium borohydride, lithium borohydride, compounds containing the $Sn^{+2}$ ion such as tin(II)chloride, sulfite compounds, hydrazine, zinc-mercury amalgum, diisobutylaluminum hydride (DIBAL-H), Lindlar catalyst, oxalic acid, formic acid, ascorbic acid, phosphites, hypophosphites and phosphorous acid, dithiothretol (DTT), compounds containing $Fe^{+2}$ ion such as iron(II)sulfate, carbon monoxide and the like.

The term "acid" used in the present invention refers to inorganic acid selected from hydrochloric acid, hydrobromic acid, sulfuric acid, nitric acid, phosphoric acid, sulfamic acid and the like; organic acid such as formic acid, acetic acid, trifluoro acetic acid, methane sulfonic acid, ethane sulfonic acid, benzene sulfonic acid, trifluoromethane sulfonic acid, p-toluene sulfonic acid, tartaric acid, mandelic acid, malic acid, maleic acid, succinic acid, malonic acid, oxalic acid, dibenzoyl tararic acid, lactic acid, cinnamic acid and the like.

The first aspect of the present invention provides an improved process for the preparation of (3R,3aS,6aR)-hexahydrofuro[2,3-b]furan-3-ol compound of formula-2, comprising of:
  a) Reacting L-Ascorbic acid compound of formula-3 with 2,2-dimethoxypropane in a suitable solvent to provide 5,6-O-isopropylidene-L-ascorbic acid compound of formula-4,
  b) oxidizing compound of formula-4 with a suitable oxidizing agent in presence of calcium carbonate in a suitable solvent to provide calcium salt of 3,4-O-isopropylidene-L-threonic acid compound of formula-5,
  c) reacting compound of formula-5 with sodium hypochloride in presence of acetic acid and sodium acetate in a suitable solvent to provide (S)-2,2-dimethyl-1,3-dioxolane-4-carbaldehyde compound of formula-6,
  d) reacting compound of formula-6 with ethyl-2-(diethoxyphosphoryl)acetate compound of formula-7 in presence of a base in a suitable solvent to provide α,β-unsaturated ester (R,E)-ethyl 3-(2,2-dimethyl-1,3-dioxolan-4-yl)acrylate compound of formula-8,
  e) reacting ester compound of formula-8 with nitromethane in presence of a base in a suitable solvent to provide (R)-ethyl 3-((R)-2,2-dimethyl-1,3-dioxolan-4-yl)-4-nitrobutanoate compound of formula-9,
  f) reducing compound of formula-9 with a suitable reducing agent in presence of lithium bromide in a suitable solvent to provide (R)-3-((R)-2,2-dimethyl-1,3-dioxolan-4-yl)-4-nitrobutan-1-ol compound of formula-10,
  g) cyclization of compound of formula-10 in presence of a suitable base and a suitable inorganic acid in a suitable solvent to provide (3R,3aS,6aR)-hexahydrofuro[2,3-b]furan-3-ol compound of formula-2.
Wherein
in step-c), d), e) and f) the suitable solvent is selected from ester solvents, ether solvents, chloro solvents, hydrocarbon solvents, ketone solvents and alcohol solvents or mixture thereof;
in step-g) the suitable solvent is selected from ester solvents, ether solvents, chloro solvents; hydrocarbon solvents and ketone solvents or mixture thereof;
in step-d), e) and g) the suitable base is selected from organic or inorganic base;
in step-f) a suitable reducing agent is selected from Lithium aluminum hydride (LiAlH4), hydroquinone, sodium amalgum, diborane, sodium borohydride, lithium borohydride, compounds containing the $Sn^{+2}$ ion such as tin(II)chloride, sulfite compounds, hydrazine, zinc-mercury amalgum, diisobutylaluminum hydride (DIBAL-H), Lindlar catalyst, dithiothretol (DTT), compounds containing $Fe^{+2}$ ion such as iron(II)sulfate, carbon monoxide and the like, in step-g) a suitable inorganic acid is selected from hydrochloric acid, hydrobromic acid, sulfuric acid, nitric acid, phosphoric acid, sulfamic acid and the like.

The preferred embodiment of the present invention provides an improved process for the preparation of (3R,3aS,6aR)-hexahydrofuro[2,3-b]furan-3-ol compound of formula-2, comprising of:
a) Reacting L-Ascorbic acid compound of formula-3 with 2,2-dimethoxypropane in acetone provides 5,6-O-isopropylidene-L-ascorbic acid compound of formula-4,
b) oxidizing compound of formula-4 with hydrogen peroxide in presence of calcium carbonate in water followed by treatment with manganese dioxide provides calcium salt of 3,4-O-isopropylidene-L-threonic acid compound of formula-5,
c) reacting compound of formula-5 with sodium hypochloride in presence of acetic acid and sodium acetate in water provides (S)-2,2-dimethyl-1,3-dioxolane-4-carbaldehyde compound of formula-6,
d) reacting compound of formula-6 with ethyl-2-(diethoxyphosphoryl)acetate compound of formula-7 in presence of potassium tert-butoxide in dichloromethane provides α,β-unsaturated ester (R,E)-ethyl 3-(2,2-dimethyl-1,3-dioxolan-4-yl)acrylate compound of formula-8,
e) reacting ester compound of formula-8 with nitromethane in presence of 1,8-Diazabicyclo[5.4.0]undec-7-ene in acetonitrile provides (R)-ethyl 3-((R)-2,2-dimethyl-1,3-dioxolan-4-yl)-4-nitrobutanoate compound of formula-9,
f) reducing compound of formula-9 with sodium borohydride in presence of lithium bromide in tetrahydrofuran provides (R)-3-((R)-2,2-dimethyl-1,3-dioxolan-4-yl)-4-nitrobutan-1-ol compound of formula-10,
g) cyclization of compound of formula-10 in presence of potassium tert-butoxide and sulfuric acid in et and water provides (3R,3aS,6aR)-hexahydrofuro[2,3-b]furan-3-ol compound of formula-2.

Alternatively, the compound of formula-10 of step-f) can be prepared by reducing compound of formula-9 in presence of lithium borohydride in tetrahydrofuran.

The compound of formula-2 of step-g) can also be prepared by cyclization of compound of formula-10 in presence of sodium hydroxide and sulfuric acid in water.

U.S. Pat. No. 7,126,015 B2 discloses the cyclisation of compound of formula-10 in presence of potassium tert-butoxide in isopropanol followed by reaction with concentrated hydrochloric acid in isopropanol results in the formation of mixture of compound of formula-2 in a ratio of 78:22. Whereas, the process of the present invention involves the cyclisation of (R)-3-((R)-2,2-dimethyl-1,3-dioxolan-4-yl)-4-nitrobutan-1-ol compound of formula-10 in presence of sodium hydroxide or potassium tert-butoxide in presence of sulfuric acid in water results in the formation of required specific isomer i,e. (3R,3aS,6aR)-hexahydrofuro[2,3-b]furan-3-ol compound of formula-2 with good yield and purity which makes the process more simple, economically viable and advantageous over the process disclosed in U.S. Pat. No. 7,126,015 B2. Hence, the process of the present invention is advantageous over the process disclosed in prior-art such as U.S. Pat. No. 7,126,015 B2.

The second aspect of the present invention is to provide an improved process for the preparation of (R,E)-ethyl-3-(2,2-dimethyl-1,3-dioxolan-4-yl)acrylate compound of formula-8, comprising of reacting the compound of formula-6 with ethyl-2-(diethoxyphosphoryl) acetate compound of formula-7 in presence of a base in a suitable solvent to provide α,β-unsaturated ester (R,E)-ethyl 3-(2,2-dimethyl-1,3-dioxolan-4-yl)acrylate compound of formula-8.

Wherein, the suitable base and solvent used are same as defined in step-d) of the first aspect of the present invention.

The preferred embodiment of the present invention provides an improved process for the preparation of (R,E)-ethyl-3-(2,2-dimethyl-1,3-dioxolan-4-yl)acrylate compound of formula-8, comprising of reacting compound of formula-6 with ethyl-2-(diethoxyphosphoryl) acetate compound of formula-7 in presence of potassium tert-butoxide in dichloromethane provides α,β-unsaturated ester i.e, (R,E)-ethyl 3-(2,2-dimethyl-1,3-dioxolan-4-yl)acrylate compound of formula-8.

The third aspect of the present invention is to provide an improved process for the preparation of (R)-ethyl-3-((R)-2,2-dimethyl-1,3-dioxolan-4-yl)-4-nitrobutanoate compound of formula-9, comprising of reacting ester compound of formula-8 with nitromethane in presence of a base in a suitable solvent to provide (R)-ethyl 3-((R)-2,2-dimethyl-1,3-dioxolan-4-yl)-4-nitrobutanoate compound of formula-9.

Wherein, the suitable base and solvent used are same as defined in step-e) of the first aspect of the present invention.

The preferred embodiment of the present invention provides an improved process for the preparation of (R)-ethyl-3-((R)-2,2-dimethyl-1,3-dioxolan-4-yl)-4-nitrobutanoate compound of formula-9, comprising of reacting ester compound of formula-8 with nitromethane in presence of tetrabutylammonium fluoride in tetrahydrofuran provides (R)-ethyl 3-((R)-2,2-dimethyl-1,3-dioxolan-4-yl)-4-nitrobutanoate compound of formula-9.

The forth aspect of the present invention is to provide an alternate process for the preparation of (3R,3aS,6aR)-hexahydrofuro[2,3-b]furan-3-ol compound of formula-2, comprising of:
a) Treating (R)-ethyl 3-((R)-2,2-dimethyl-1,3-dioxolan-4-yl)-4-nitrobutanoate compound of formula-9 with a suitable inorganic acid in a suitable solvent to provide (5S)-5-(hydroxymethyl)-4-(nitromethyl)dihydrofuran-2(3H)-one compound of formula-11,
b) reducing compound of formula-11 in presence of a suitable reducing agent in a suitable solvent to provide (2S)-3-(nitromethyl)pentane-1,2,5-triol compound of formula-12,
c) cyclizating of compound of formula-12 in presence of a suitable base and a suitable inorganic acid in a suitable solvent to provide (3R,3aS,6aR)-hexahydrofuro[2,3-b]furan-3-ol compound of formula-2.
Wherein,
in step-a), b) and c) the suitable solvent is selected from ester solvents, ether solvents, chloro solvents, hydrocarbon solvents, ketone solvents and alcohol solvents or mixture thereof;
in step-a) and c) the suitable inorganic acid is selected from hydrochloric acid, hydrobromic acid, sulfuric acid, nitric acid, phosphoric acid, sulfamic acid and the like;
in step-b) a suitable reducing agent is same as defined in step-f) of first aspect of the present invention.
in step-c) a suitable base is selected from organic or inorganic base.

The above process can be prepared by one pot process without isolating compounds of formula-11 and formula-12.

The preferred embodiment of the present invention provides a process for the preparation of (3R,3aS,6aR)-hexahydrofuro[2,3-b]furan-3-ol compound of formula-2, comprising of:
a) Treating (R)-ethyl 3-((R)-2,2-dimethyl-1,3-dioxolan-4-yl)-4-nitrobutanoate compound of formula-9 with concentrated hydrochloric acid in methanol provides (5S)-5-(hydroxymethyl)-4-(nitromethyl)dihydrofuran-2 (3H)-one compound of formula-11, b) reducing compound of formula-11 in-situ in presence of sodium borohydride in a mixture of tetrahydrofuran and methanol provides (2S)-3-(nitromethyl)pentane-1,2,5-triol compound of formula-12, c) cyclizating compound of formula-12 in-situ in presence of potassium tert-butoxide and concentrated hydrochloric acid in methanol followed by treating with triethylamine provides (3R,3aS,6aR)-hexahydrofuro[2,3-b]furan-3-ol compound of formula-2.

The fifth aspect of the present invention is to provide a process for the preparation of amorphous [(1S,2R)-3-[[(4-aminophenyl)sulfonyl](2-methylpropyl)amino]-2-hydroxy-1-(phenylmethyl)propyl]carbamic acid (3R,3aS,6aR)-hexahydrofuro[2,3-b]furan-3-yl ester compound of formula-1, comprising of:

a) Reacting (3R,3aS,6aR)-hexahydrofuro[2,3-b]furan-3-ol compound of formula-2 with N,N'-disuccinimidyl carbonate compound of formula-13 in presence of suitable base in a suitable solvent to provide 2,5-dioxopyrrolidin-1-yl (3R,3aS,6aR)-hexahydrofuro[2,3-b]furan-3-yl carbonate compound of formula-14, b) reacting compound of formula-14 with 4-amino-N-((2R,3S)-3-amino-2-hydroxy-4-phenylbutyl)-N-isobutylbenzenesulfonamide compound of formula-15 in presence of a base in a suitable alcohol solvent to provide [(1S,2R)-3-[[(4-aminophenyl) sulfonyl](2-methylpropyl)amino]-2-hydroxy-1-(phenylmethyl)propyl]carbamic acid (3R,3aS,6aR)-hexahydrofuro[2,3-b]furan-3-yl ester compound of formula-1, c) purifying the compound of formula-1 in a suitable solvent provides amorphous [(1S,2R)-3-[[(4-aminophenyl)sulfonyl](2-methylpropyl)amino]-2-hydroxy-1-(phenyl methyl)propyl]carbamic acid (3R,3aS,6aR)-hexahydrofuro[2,3-b]furan-3-yl ester compound of formula-1.

Wherein, in step-b) a suitable solvent is selected from methanol, ethanol, n-propanol, isopropanol, n-butanol, isobutanol, tert-butanol and the like or mixture thereof.

The preferred embodiment of the present invention provides a process for the preparation of Amorphous [(1S,2R)-3-[[(4-aminophenyl)sulfonyl](2-methylpropyl)amino]-2-hydroxy-1-(phenylmethyl)propyl]carbamic acid (3R,3aS,6aR)-hexahydrofuro[2,3-b]furan-3-yl ester compound of formula-1, comprising of:

a) Reacting (3R,3aS,6aR)-hexahydrofuro[2,3-b]furan-3-ol compound of formula-2 with N,N'-disuccinimidyl carbonate compound of formula-13 in presence of pyridine in dichloromethane provides 2,5-dioxopyrrolidin-1-yl (3R,3aS,6aR)-hexahydrofuro[2,3-b]furan-3-yl carbonate compound of formula-14, b) reacting compound of formula-14 with 4-amino-N-((2R,3S)-3-amino-2-hydroxy-4-phenylbutyl)-N-isobutylbenzenesulfonamide compound of formula-15 in presence of triethylamine in methanol provides [(1S,2R)-3-[[(4-aminophenyl)sulfonyl](2-methyl propyl)amino]-2-hydroxy-1-(phenylmethyl)propyl]carbamic acid (3R,3aS,6aR)-hexahydrofuro[2,3-b]furan-3-yl ester compound of formula-1, c) purifying the compound of formula-1 in a mixture of dichloromethane and methanol provides amorphous [(1S,2R)-3-[[(4-aminophenyl)sulfonyl](2-methylpropyl)amino]-2-hydroxy-1-(phenylmethyl)propyl]carbamic acid (3R,3aS,6aR)-hexahydrofuro[2,3-b]furan-3-yl ester compound of formula-1.

The another preferred embodiment of the present invention provides a process for the preparation of Amorphous [(1S,2R)-3-[[(4-aminophenyl)sulfonyl](2-methylpropyl)amino]-2-hydroxy-1-(phenylmethyl)propyl]carbamic acid (3R,3aS,6aR)-hexahydrofuro[2,3-b]furan-3-yl ester compound of formula-1, comprising of:

a) Reacting (3R,3aS,6aR)-hexahydrofuro[2,3-b]furan-3-ol compound of formula-2 with N,N'-disuccinimidyl carbonate compound of formula-13 in presence of pyridine in dichloromethane provides 2,5-dioxopyrrolidin-1-yl (3R,3aS,6aR)-hexahydrofuro[2,3-b]furan-3-yl carbonate compound of formula-14, b) purifying the obtained compound using n-hexane and methanol provides pure compound of formula-14, c) reacting compound of formula-14 with 4-amino-N-((2R,3S)-3-amino-2-hydroxy-4-phenylbutyl)-N-isobutylbenzenesulfonamide compound of formula-15 in presence of triethylamine in methanol provides [(1S,2R)-3-[[(4-aminophenyl)sulfonyl](2-methyl propyl)amino]-2-hydroxy-1-(phenylmethyl)propyl]carbamic acid (3R,3aS,6aR)-hexahydrofuro[2,3-b]furan-3-yl ester compound of formula-1, d) purifying the compound of formula-1 in a mixture of dichloromethane and methanol and followed by slurrying the obtained compound from cyclohexane provides pure amorphous [(1S,2R)-3-[[(4-aminophenyl)sulfonyl](2-methylpropyl)amino]-2-hydroxy-1-(phenylmethyl)propyl]carbamic acid (3R,3aS,6aR)-hexahydrofuro[2,3-b]furan-3-yl ester compound of formula-1.

The sixth aspect of the present invention provides a one-pot process for the preparation of (3R,3aS,6aR)-hexahydrofuro[2,3-b]furan-3-ol compound of formula-2, comprising of:

a) Reacting L-Ascorbic acid compound of formula-3 with 2,2-dimethoxypropane in a suitable solvent to provide 5,6-O-isopropylidene-L-ascorbic acid compound of formula-4, b) oxidizing compound of formula-4 in-situ with a suitable oxidizing agent in presence of sodium hydroxide in a suitable solvent to provide sodium salt of 3,4-O-isopropylidene-L-threonic acid compound of formula-16, c) reacting compound of formula-16 in-situ with a suitable alkylating agent in presence of a suitable base in a suitable solvent to provide (R)-methyl-2-((S)-2,2-dimethyl-1,3-dioxolan-4-yl)-2-hydroxyacetate compound of formula-17, d) reducing compound of formula-17 with a suitable reducing agent in a suitable solvent to provide (S)-1-((S)-2,2-dimethyl-1,3-dioxolan-4-yl)ethane-1,2-diol compound of formula-18, e) reacting compound of formula-18 in-situ with sodium periodate in presence of suitable base in a suitable solvent to provide (S)-2,2-dimethyl-1,3-dioxolane-4-carbaldehyde compound of formula-6, f) reacting compound of formula-6 in-situ with ethyl-2-(diethoxyphosphoryl)acetate compound of formula-7 in presence of a base in a suitable solvent to provide α,β-unsaturated ester (R,E)-ethyl 3-(2,2-dimethyl-1,3-dioxolan-4-yl)acrylate compound of formula-8, g) reacting ester compound of formula-8 in-situ with nitromethane in presence of a base in a suitable solvent to provide (R)-ethyl 3-((R)-2,2-dimethyl-1,3-dioxolan-4-yl)-4-nitrobutanoate compound of formula-9, h) reducing compound of formula-9 in-situ with a suitable reducing agent in presence of lithium bromide in a suitable solvent to provide (R)-3-((R)-2,2-dimethyl-1,3-dioxolan-4-yl)-4-nitrobutan-1-ol compound of formula-10, i) cyclization of compound of formula-10 in-situ in presence of a suitable base and a suitable inorganic acid in a suitable solvent to provide (3R,3aS,6aR)-hexahydrofuro[2,3-b]furan-3-ol compound of formula-2.

Wherein in step-a) to i) the suitable solvent is selected from ester solvents, ether solvents, chloro solvents, hydrocarbon solvents, ketone solvents, alcohol solvents, polar solvents such as water or mixture thereof;

in step-c), e), f), g) and i) the suitable base is selected from organic or inorganic base;

in step-d) & h) the suitable reducing agent is selected from Lithium aluminum hydride (LiAlH4), hydroquinone, sodium amalgum, diborane, sodium borohydride, lithium borohydride, compounds containing the $Sn^{+2}$ ion such as tin(II)chloride, sulfite compounds, hydrazine, zinc-mercury amalgum, diisobutylaluminum hydride (DIBAL-H), Lindlar catalyst, dithiothretol (DTT), compounds containing $Fe^{+2}$ ion such as iron(II)sulfate, carbon monoxide and the like, in step-i) a suitable inorganic acid is selected from hydrochloric acid, hydrobromic acid, sulfuric acid, nitric acid, phosphoric acid, sulfamic acid and the like.

The preferred embodiment of the present invention provides a one-pot process for the preparation of (3R,3aS,6aR)-hexahydrofuro[2,3-b]furan-3-ol compound of formula-2, comprising of:

a) Reacting L-Asorbic acid compound of formula-3 with 2,2-dimethoxypropane in acetone to provide 5,6-O-isopropylidene-L-ascorbic acid compound of formula-4, b) oxidizing compound of formula-4 in-situ with hydrogen peroxide in presence of sodium hydroxide in water to provide sodium salt of 3,4-O-isopropylidene-L-threonic acid compound of formula-16, c) reacting compound of formula-16 in-situ with dimethyl sulfate in presence of sodium bicarbonate in dichloromethane to provide (R)-methyl-2-((S)-2,2-dimethyl-1,3-dioxolan-4-yl)-2-hydroxyacetate compound of formula-17, d) reducing the compound of formula-17 with sodium borohydride in a mixture of dichloromethane and methanol to provide (S)-1-((S)-2,2-dimethyl-1,3-dioxolan-4-yl)ethane-1,2-diol compound of formula-18, e) reacting compound of formula-18 in-situ with sodium periodate in presence of sodium bicarbonate in dichloromethane to provide (S)-2,2-dimethyl-1,3-dioxolane-4-carbaldehyde compound of formula-6, f) reacting compound of formula-6 in-situ with ethyl-2-(diethoxyphosphoryl)acetate compound of formula-7 in presence of potassium tert-butoxide in dichloromethane provides α,β-unsaturated ester (R,E)-ethyl 3-(2,2-dimethyl-1,3-dioxolan-4-yl)acrylate compound of formula-8, g) reacting ester compound of formula-8 in-situ with nitromethane in presence of tetrabutylammoniumfluoride in tetrahydrofuran provides (R)-ethyl 3-((R)-2,2-dimethyl-1,3-dioxolan-4-yl)-4-nitrobutanoate compound of formula-9, h) reducing compound of formula-9 in-situ with sodium borohydride in presence of lithium bromide in tetrahydrofuran provides (R)-3-((R)-2,2-dimethyl-1,3-dioxolan-4-yl)-4-nitrobutan-1-ol compound of formula-10, i) cyclization of compound of formula-10 in-situ in presence of potassium tert-butoxide and sulfuric acid in tetrahydrofuran and water provides (3R,3aS,6aR)-hexahydrofuro[2,3-b]furan-3-ol compound of formula-2.

The compounds of formula-7 and formula-13 can be prepared by the process known in the art.

We have repeated the process for the preparation of Darunavir which was analogously disclosed in U.S. Pat. No. 6,248,775 B2 and characterized the PXRD and IR of the obtained compound of formula-1. We have found that, the PXRD and IR patterns of compound of formula-1 obtained from the present invention are well matching with the PXRD and IR patterns of compound of formula-1 as per the process disclosed in U.S. Pat. No. 6,248,775 B2. The said PXRD & IR patterns have been depicted in FIG. 1 & FIG. 2.

The amorphous compound of formula-1 obtained according to the present invention can be useful in the preparation of pharmaceutical composition.

P-XRD Method of Analysis:

PXRD analysis of compound of formula-1 produced by the present invention can be carried out using BRUKER/AXS X-Ray diffractometer using Cu Kα radiation of wavelength 1.5406 A° and continuous scan speed of 0.03°/min.

IR spectra of compound of formula-1 was recorded on a Perkin-Elmer FTIR spectrometer The compound of formula-1 produced by the present invention can be further micronized or milled to get the desired particle size to achieve desired solubility profile based on different forms of pharmaceutical composition requirements. Techniques that may be used for particle size reduction include, but not limited to ball, roller and hammer mills, and jet mills. Milling or micronization may be performed before drying, or after the completion of drying of the product.

The present invention is schematically represented as below:

Scheme-I:

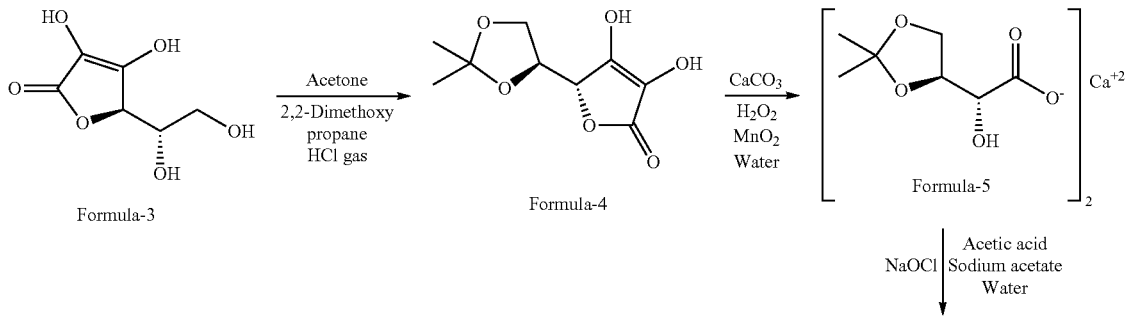

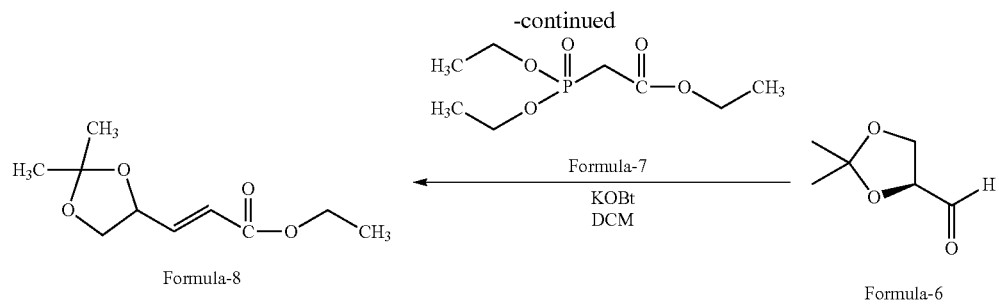
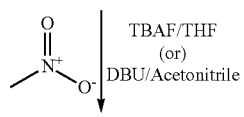
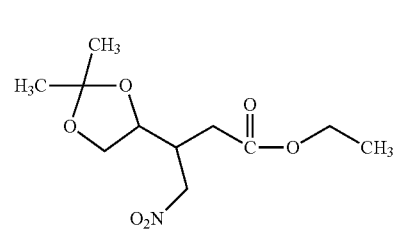
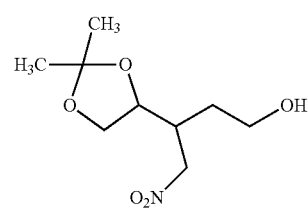
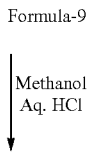
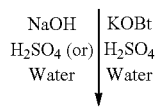
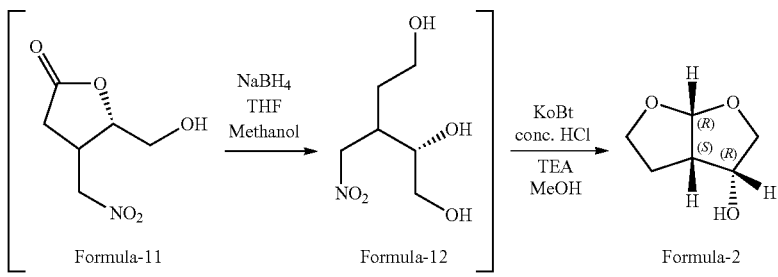
Scheme-II:
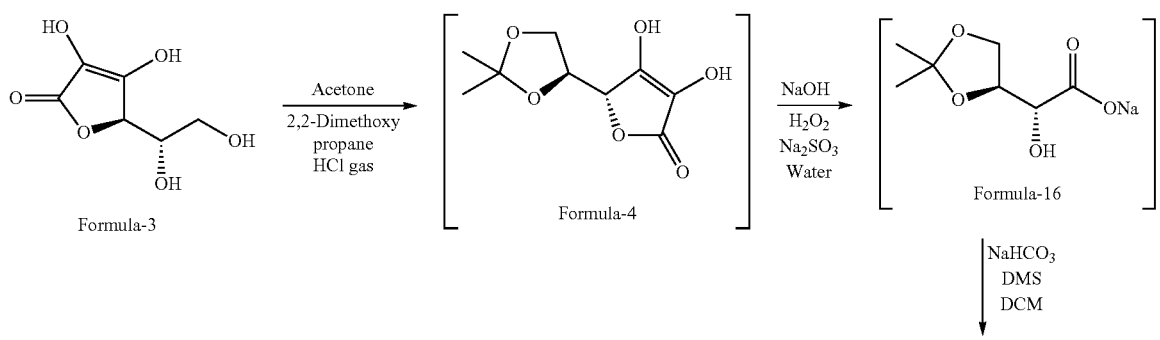

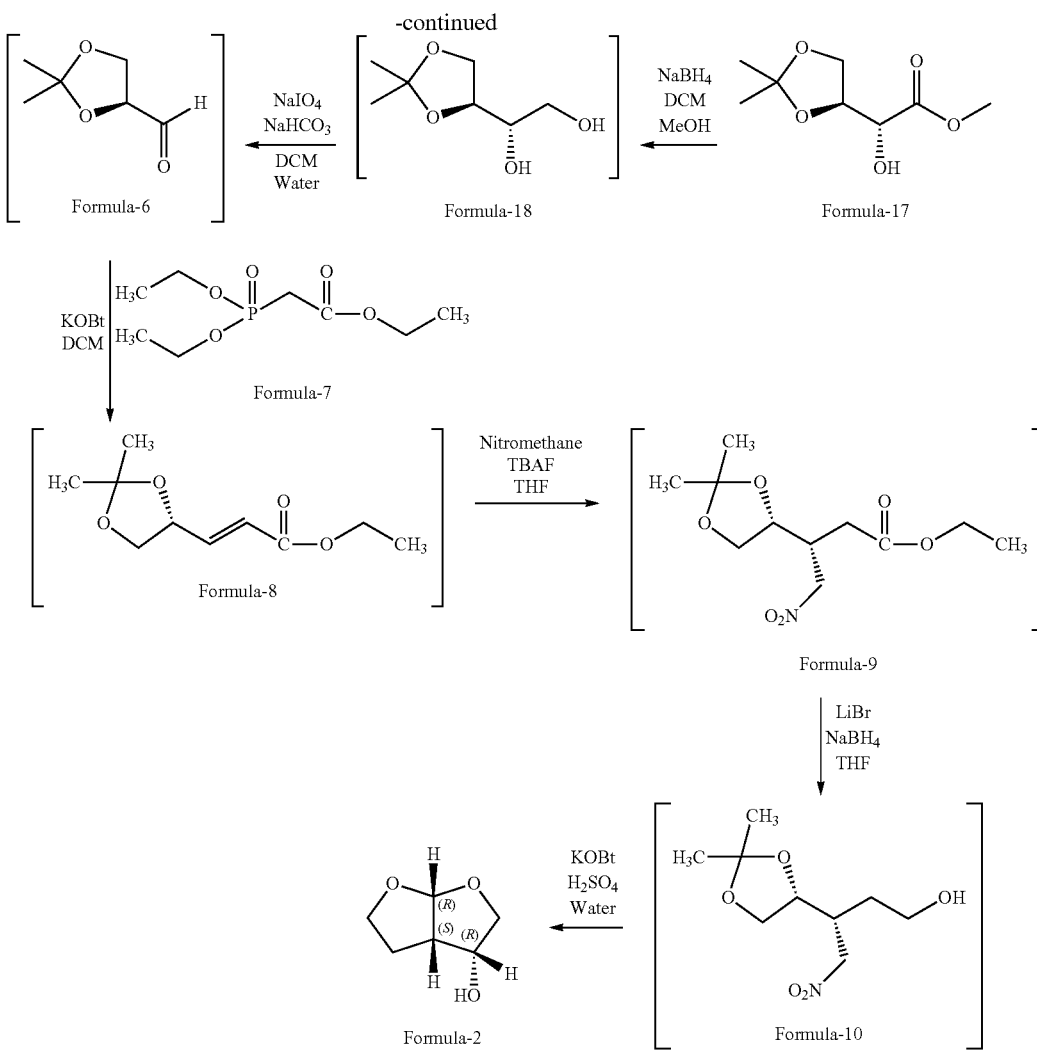
Scheme-III:
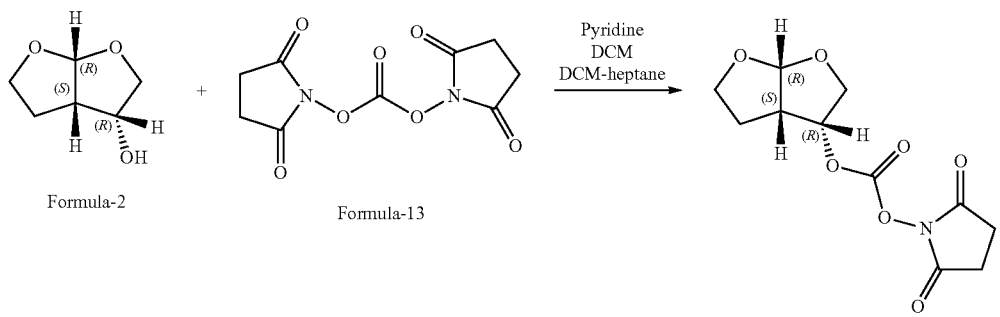
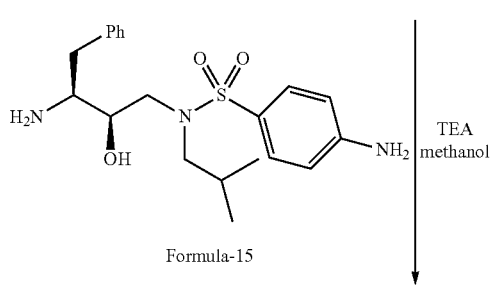

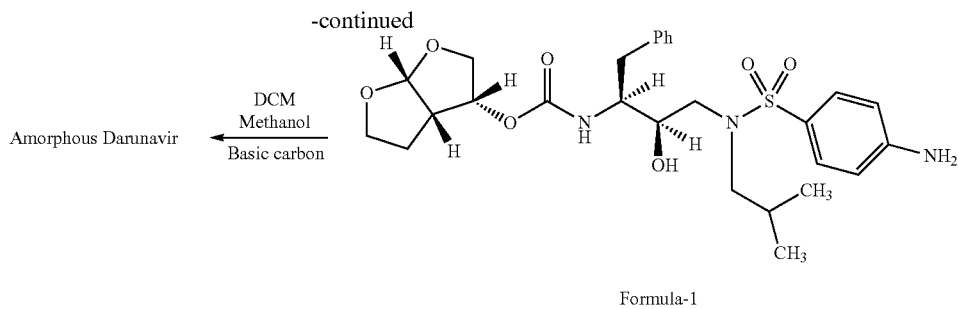

Formula-1

The process described in the present invention was demonstrated in examples illustrated below. These examples are provided as illustration only and therefore should not be construed as limitation of the scope of the invention.

EXAMPLES

Example-1: Preparation of 5,6-O-isopropylidene-L-ascorbic acid (Formula-4)

A mixture of L-Ascorbic acid compound of formula-3 (50 gm) and acetone (250 ml) was stirred for 15 minutes. 2,2-Dimethoxy propane (62.5 ml) was added to the reaction mixture. Acidified the reaction mixture by using HCl gas and stirred for 4 hrs at 25-30° C. Cooled the reaction mixture to 5-10° C. and stirred for 45 minutes at the same temperature. The precipitated solid was filtered, washed with acetone and dried to get the title compound.

Yield: 50 gm; M.R: 205-210° C.

Example-2: Preparation of Calcium-3,4-O-isopropylidene-L-threonic acid (Formula-5)

Calcium carbonate (115.5 gm) was added lot wise to the mixture of 5,6-O-isopropylidene-L-ascorbic acid compound of formula-4 (100 gm) and water (300 ml). Aqueous hydrogen peroxide (126 ml and water 84 ml) was added slowly to the reaction mixture at 25-30° C. and stirred for 5 hrs at the same temperature. Heated the reaction mixture to 55-60° C. and stirred for 2 hrs at the same temperature. Manganese dioxide (1.2 gm) was added to the reaction mixture at 55-60° C. and stirred for 2 hrs at the same temperature. Cooled the reaction mixture to 25-30° C. Filtered the undissolved salts through hyflow bed and washed with water. Some portion of water was distilled off from the filtrate. Cooled the reaction mixture to 25-30° C. Acetone was slowly added to the reaction mixture. Cooled the reaction mixture to 0-5° C. and stirred for 4 hrs at the same temperature. The precipitated solid was filtered, washed with acetone and dried to get the title compound.

Yield: 55 gm; M.R: 260-266° C., SOR=+29.311 (c=0.9% water).

Example-3: Preparation of (S)-2,2-dimethyl-1,3-dioxolane-4-carbaldehyde (Formula-6)

Sodium acetate (99 gm) and acetic acid (119.8 gm) were added to the mixture of calcium salt of 3,4-O-isopropylidene-L-threonic acid compound of formula-5 (65 gm) and water (520 ml). Heated the reaction mixture to 50-55° C. Sodium hypochlorite (284 ml) was slowly added to the reaction mixture at 50-55° C. and stirred for 4 hrs at the same temperature. Cooled the reaction mixture to 25-30° C. Basify the reaction mixture by slowly adding sodium carbonate (105 gm) and stirred at 25-30° C. for 15 minutes. The unwanted salt formed was filtered and washed with the mixture of dichloromethane and methanol. Both the organic and aqueous layers were separated from the filtrate. Sodium chloride (130 gm) was added to aqueous layer and extracted the aqueous layer with the mixture of dichloromathane and methanol. Combined the organic layers and distilled off the solvent completely from the organic layer under reduced pressure to get the title compound. Yield: 25 gm.

Example-4: Preparation of (R,E)-ethyl 3-(2,2-dimethyl-1,3-dioxolan-4-yl)acrylate (Formula-8)

Potassium tert-butoxide (20 gm) was added to the mixture of dichloromethane (200 ml) and triethyl phosphonoacetate compound of formula-7 (27.5 gm) at 0-5° C. under nitrogen atmosphere. A solution of (S)-2,2-dimethyl-1,3-dioxolane-4-carbaldehyde compound of formula-6 (20 gm in 50 ml) in dichloromethane was slowly added to the reaction mixture at 0-5° C. and stirred the reaction mixture for 4 hrs. Distilled off the solvent from the reaction mixture completely under reduced pressure at the same temperature. Ethyl acetate (50 ml) followed by aqueous sodium bicarbonate solution (4 gm dissolved in 50 ml water) were added to the reaction mixture. Both the organic and aqueous layers were separated. Distilled off the solvent completely from the organic layer under reduced pressure to get the title compound. Yield: 18 gm, SOR=−30.24° (c=1% chloroform)

Example-5: Preparation of (R)-ethyl 3-((R)-2,2-dimethyl-1,3-dioxolan-4-yl)-4-nitro butanoate (Formula-9)

A mixture of (R,E)-ethyl 3-(2,2-dimethyl-1,3-dioxolan-4-yl)acrylate compound of formula-8 (2 gm) and acetonitrile (20 ml) was cooled to 0-5° C. Nitromethane (0.67 gm) was added to the reaction mixture at 0-5° C. and stirred for 10 minutes. 1,8-Diazabicyclo[5.4.0]undec-7-ene solution (2.3 gm in 6 ml of acetonitrile) was slowly added to the reaction mixture and stirred for 25 hrs at 25-30° C. Solvent from the reaction mixture was evaporated by purging nitrogen. Ethyl acetate and water was added to the reaction mixture. Both the organic and aqueous layers were separated. The aqueous layer was extracted with ethyl acetate. Combined the organic layers and washed with aq.HCl solution followed by with aqueous sodium bicarbonate solution. The solvent from the organic layer was evaporated by purging nitrogen to get the title compound. Yield: 2 gm Example-6: Preparation of (3R,3aS,6aR)-hexahydrofuro[2,3-b]furan-3-ol (Formula-2)

A mixture of sodium borohydride (0.7 gm), lithium bromide (1.6 gm) and tetrahydrofuran (50 ml) was cooled to 0-5° C. (R)-Ethyl 3-((R)-2,2-dimethyl-1,3-dioxolan-4-yl)-4-nitrobutanoate compound of formula-9 (5 gm) was added to the reaction mixture at 0-5° C. Raised the temperature of the reaction mixture to 25-30° C. and stirred for 35 hrs at the same temperature. Potassium tert-butoxide (2 gm) was added to the above reaction mixture at 25-30° C. under nitrogen atmosphere and stirred for 20 minutes. The reaction mixture was slowly added to the sulfuric acid solution (2.7 ml in 6 ml of water) at 0-5° C. and stirred for 20 minutes. Raised the temperature of the reaction mixture to 25-30° C. and stirred for 5 hrs at the same temperature. Cooled the reaction mixture to 0-5° C. Neutralized the reaction mixture by adding triethylamine. Filtered the reaction mixture through hyflow bed, washed with tetrahydrofuran. Distilled off the solvent from the filtrate under reduced pressure. Ethyl acetate was added to the obtained compound at 25-30° C. and stirred for 5 minutes. Filtered the undissolved salt through hyflow bed and washed with ethyl acetate. Distilled off the filtrate completely under reduced pressure to get the title compound. Yield: 1.5 gm Example-7: Preparation of (R)-ethyl 3-((R)-2,2-dimethyl-1,3-dioxolan-4-yl)-4-nitrobutanoate (Formula-9)

A mixture of (R,E)-ethyl 3-(2,2-dimethyl-1,3-dioxolan-4-yl)acrylate compound of formula-8 (25 gm) and tetrahydrofuran (50 ml) was cooled to 0-5° C. Nitromethane (9 gm) was added to the reaction mixture at 0-5° C. and stirred for 5 minutes. Tetrabutyl ammonium fluoride solution (39 gm in 250 ml tetrahydrofuran) was slowly added to the reaction mixture at 0-5° C. and stirred the reaction mixture for 4 hrs at the same temperature. The solvent from the reaction mixture was evaporated by purging nitrogen. Ethyl acetate followed by aqueous sodium bicarbonate solution (4 gm in 30 ml of water) were added to the reaction mixture. Both the organic and aqueous layers were separated. The solvent from the organic layer was evaporated by purging nitrogen and purified by column chromatography using cyclohexane and ethylacetate as eluent to get the title compound. Yield: 25 gm Example-8: Preparation of (3R,3aS,6aR)-hexahydrofuro[2,3-b]furan-3-ol (Formula-2)

Hydrochloric acid (4 ml) was added to the mixture of (R)-ethyl 3-((R)-2,2-dimethyl-1,3-dioxolan-4-yl)-4-nitrobutanoate compound of formula-9 (10 gm) and methanol (100 ml) at 25-30° C. and stirred for 3 hrs at the same temperature. Sodium bicarbonate (12 gm) was added to the reaction mixture at 25-30° C. and stirred for 15 minutes at 25-30° C. Filtered the reaction mixture and washed with methanol. Distilled off the solvent completely under reduced pressure. Sodium borohydride (4.3 gm) and tetrahydrofuran (50 ml) were added to the obtained compound at 25-30° C. Heated the reaction mixture to 65-70° C. Methanol (25 ml) was added to the reaction mixture at 65-70° C. and stirred for 3 hrs at the same temperature. Cooled the reaction mixture to 25-30° C. Methanol (25 ml) and potassium tert-butoxide (5 gm) were added to the reaction mixture at 25-30° C. and stirred for 10 minutes. The reaction mixture was added to the pre-cooled mixture of methanol (25 ml) and hydrochloric acid (10 ml) at 0-5° C. Raised the reaction mixture temperature to 25-30° C. and stirred for 3 hrs at the same temperature. Cooled the reaction mixture to 0-5° C. Neutralized the reaction mixture by adding triehtylamine at 0-5° C. Raised the reaction mixture temperature to 25-30° C. Filtered the reaction mixture through hyflow bed and washed with ethyl acetate. Distilled off the solvent from the filtrate. Ethyl acetate was added to the obtained compound and stirred for 5 minutes. Filtered the reaction mixture through hyflow bed and washed with ethyl acetate. Distilled off the solvent from the reaction mixture to get the title compound. Yield: 2.5 gm Example-9: Preparation of Preparation of (R)-3-((R)-2,2-dimethyl-1,3-dioxolan-4-yl)-4-nitrobutan-1-ol (Formula-10)

A mixture of (R)-ethyl 3-((R)-2,2-dimethyl-1,3-dioxolan-4-yl)-4-nitrobutanoate compound of formula-9 (20 gm) and tetrahydrofuran (200 ml) was cooled to 0-5° C. under nitrogen atmosphere. Lithium borohydride (60 ml) was added to the reaction mixture at 0-5° C. Raised the temperature of the reaction mixture to 25-30° C. and stirred for 18 hrs at the same temperature. Cooled the reaction mixture to 0-5° C. Aqueous ammonium chloride solution (30 gm in 100 ml water) was added to the reaction mixture at 0-5° C. Raised the temperature of the reaction mixture to 25-30° C. Ethyl acetate was added to the reaction mixture. Both the organic and aqueous layers were separated. The aqueous layer was extracted with ethyl acetate. Combined the organic layers and washed with aq.sodium chloride solution. The solvent from the organic layer was evaporated by purging nitrogen to get the title compound. Yield: 9 gm Example-10: Preparation of (3R,3aS,6aR)-hexahydrofuro[2,3-b]furan-3-ol (Formula-2)

A mixture of sodium hydroxide (0.4 gm) and water (7 ml) was cooled to 5-10° C. (R)-3-((R)-2,2-dimethyl-1,3-dioxolan-4-yl)-4-nitrobutan-1-ol compound of formula-10 (1.8 gm) was added to the reaction mixture at 0-5° C. Sulfuric acid solution (1.2 ml in 8 ml of water) was slowly added to the reaction mixture at 5-10° C. and stirred for 15 minutes at the same temperature. Raised the temperature of the reaction mixture to 25-30° C. and stirred for 2 hrs at the same temperature. Sodium chloride (10 gm) and dichloromethane were added to the reaction mixture. The organic and aqueous layers were separated and the aqueous layer was extracted with dichloromethane. Distilled off the solvent completely from the organic layer under reduced pressure to get the title compound. Yield: 0.6 gm Example-11: Preparation of 2,5-dioxopyrrolidin-1-yl (3R,3aS,6aR)-hexahydrofuro[2,3-b]furan-3-yl carbonate (Formula-14)

N,N'-Disuccinimidyl carbonate compound of formula-13 (148 gm) was added to the mixture of (3R,3aS,6aR)-hexahydrofuro[2,3-b]furan-3-ol compound of formula-2 (50 gm) and dichloromethane (500 ml) at 25-30° C. Pyridine (78 ml) was added to the reaction mixture at 25-30° C. Heated the reaction mixture at 40-45° C. and stirred the reaction mixture for 17 hrs at the same temperature. Washed the reaction mixture with water followed by with sodium chloride solution. Distilled off the solvent under reduced pressure. Cooled the obtained compound to 25-30° C. Dichloromethane (100 ml) was added to the obtained compound at 25-30° C. Heated the reaction mixture to 35-40° C. N-heptane (100 ml) was slowly added to the reaction mixture. Cooled the reaction mixture to 0-5° C. and stirred for 1.5 hrs at the same temperature. Filtered the precipitated solid, washed with n-heptane and dried to get the title compound. Yield: 83 gm

Example-12: Preparation of [(1S,2R)-3-[[(4-aminophenyl)sulfonyl](2-methylpropyl) amino]-2-hydroxy-1-(phenylmethyl)propyl]carbamic acid (3R, 3aS,6aR)-hexahydrofuro [2,3-b]furan-3-yl ester (Formula-1)

2,5-dioxopyrrolidin-1-yl (3R,3aS,6aR)-hexahydrofuro[2,3-b]furan-3-yl carbonate compound of formula-14 (25 gm) was added to the mixture of 4-amino-N-((2R,3S)-3-amino-2-hydroxy-4-phenylbutyl)-N-isobutylbenzenesulfonamide compound of formula-15 (36.8 gm) and methanol (125 ml) and stirred for 15 minutes. Triethylamine (13 ml) was added to the reaction mixture at 25-30° C. and stirred for 3 hrs at the same temperature. Cooled the reaction mixture to 0-5° C. and stirred for 1.5 hrs at the same temperature. Filtered the reaction mixture, washed with methanol and dried to get the title compound. Yield: 45 gm

Example-13: Preparation of Amorphous [(1S,2R)-3-[[(4-aminophenyl)sulfonyl](2-methylpropyl)amino]-2-hydroxy-1-(phenylmethyl)propyl]carbamic acid (3R,3aS,6aR)-hexahydrofuro[2,3-b]furan-3-yl ester (Formula-1)

[(1S,2R)-3-[[(4-aminophenyl)sulfonyl](2-methylpropyl) amino]-2-hydroxy-1-(phenyl methyl)propyl]carbamic acid (3R,3aS,6aR)-hexahydrofuro[2,3-b]furan-3-yl ester (50 gm) was added to a mixture of dichloromethane (27 ml) and methanol (150 ml). Carbon (5 gm in 23 ml of methanol) was added to the reaction mixture. Heated the reaction mixture to 55-60° C. and stirred for 20 minutes at the same temperature. Filtered the reaction mixture and washed with a mixture of methanol (40 ml) and dichloromethane (6 ml). The filtrate was cooled to 0-5° C. under nitrogen atmosphere and stirred for 4 hrs at the same temperature. Filtered the precipitated solid under nitrogen atmosphere, washed with chilled methanol and dried under reduced pressure to get the title compound. Yield: 44 gm.

Figure 2:
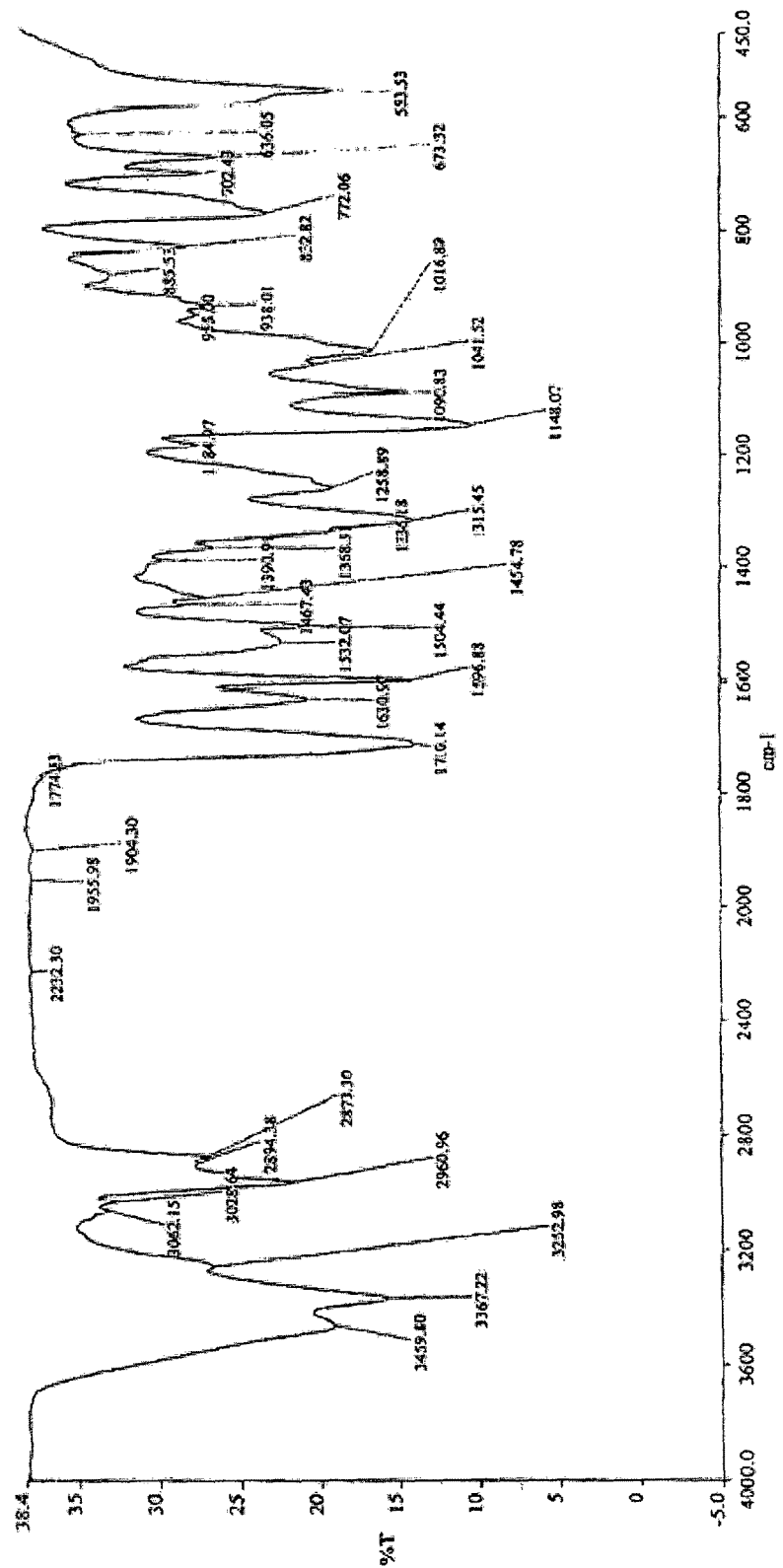
FIG. 2: Illustrates the IR pattern of [(1S,2R)-3-[[(4-aminophenyl)sulfonyl](2-methylpropyl)amino]-2-hydroxy-1-(phenylmethyl)propyl]carbamic acid (3R,3aS,6aR)-hexahydrofuro[2,3-b]furan-3-yl ester compound of formula-1.

The PXRD & IR patterns of the obtained compound is well matching with the PXRD & IR patterns of compound of formula-1 as per the process disclosed in U.S. Pat. No. 6,248,775 B2 which is depicted in FIG. 1 & FIG. 2.

Example-14: Preparation of 4-Amino-N-((2R,3S)-3-amino-2-hydroxy-4-phenylbutyl)-N-isobutyl benzenesulfonamide Ethyl acetate (250 ml) was added to 2R-hydroxy-3-[[(4-nitro phenyl)sulfonyl](2-methoxypropyl)amino]-1S-(phenyl methyl)propyl carbonic acid phenylmethyl ester (50 gins) at 25-30° C. Palladium carbon (2.5 gms) was added to the reaction mixture at 25-30° C. under hydrogen pressure. Heated the reaction mixture to 40-45° C. and stirred for 6 hours at the same temperature. Filtered the reaction mixture through hyflow bed and washed with ethyl acetate then followed by water. Distilled off the solvent completely from the organic layer under reduced pressure.

Isopropanol (200 ml) was added to the obtained solid at 25-30° C. Heated the reaction mixture to 70-75° C. and stirred for 20 minutes at the same temperature. Slowly cooled the reaction mixture to 25-30° C. further cooled to 0-5° C. and stirred for 3 hours at the same temperature. Filtered the precipitated solid, washed with isopropanol and dried to get the title compound. Yield: 26.1 gms.

Example-15: Preparation of (R)-methyl-2-((S)-2,2-dimethyl-1,3-dioxolan-4-yl)-2-hydroxyacetate Acetone (1000 ml) was added to L-ascorbic acid (200 gms) at 25-30° C. and stirred for 10 minutes at the same temperature. 2,2-dimethoxy propane (212.5 gms) was added to the reaction mixture at 25-30° C. Acidifying the reaction mixture by using hydrochloric acid gas at 25-30° C. and stirred for 4 hours at the same temperature. Cooled the reaction mixture to 0-5° C. and stirred for 45 minutes at the same temperature. Filtered the precipitated solid and washed with acetone.

Water (900 ml) and sodium hydroxide (18.2 gms) were added to the obtained solid at 25-30° C. and stirred for 10 minutes at the same temperature. Sodium bicarbonate (190.7 gms) was added portion wise to the reaction mixture at 25-30° C. Heated the reaction mixture to 45-50° C. Hydrogen peroxide (566 ml) was slowly added to the reaction mixture at 45-50° C. within 7 hours and stirred for 24 hours at the same temperature. Sodium sulfite (57.2 gms) was added to the reaction mixture at 45-50° C. and stirred for 45 minutes at the same temperature. Sodium bicarbonate (467.4 gms) was added to the reaction mixture at 25-30° C. and heated to 45-50° C. Dimethylsulphate (701.1 gms) was slowly added to the reaction mixture at 50° C. within 6 hours and stirred for 4 hours at the same temperature. Cooled the reaction mixture to 25-30° C. Filtered the reaction mixture through hyflow bed and washed with water. Obtained filtrate was extracted twice with dichloromethane. Distilled off the solvent completely from the organic layer under reduced pressure and dried to get the title compound. Yield: 148 gms.

Example-16: Preparation of (3R,3aS,6aR)-hexahydrofuro[2,3-b]furan-3-ol

Dichloromethane (1500 ml) was added to (R)-methyl-2-((S)-2,2-dimethyl-1,3-dioxolan-4-yl)-2-hydroxyacetate (150 gms) at 25-30° C. and stirred for 10 minutes at the same temperature. Sodium borohydride (45 gms) was added to the reaction mixture at 0-5° C. Methanol (150 ml) was slowly added to the reaction mixture at 0-5° C. and stirred for 30 minutes at the same temperature. Raised the temperature of the reaction mixture to 25-30° C. and stirred for 6 hours at the same temperature. Acetic acid (71 gms) was slowly added the reaction mixture at 0-5° C. and stirred for 90 minutes at the same temperature. Filtered the reaction mixture through hyflow bed and washed with dichloromethane.

Sodium bicarbonate solution (10 gm dissolved in 234 ml water) was added to the obtained filtrate at 25-30° C. Sodium periodate (308.7 gms) was added portion wise to the reaction mixture at 25-30° C. and stirred for 6 hours at the same temperature. Filtered the reaction mixture through hyflow bed and washed with dichloromethane. Distilled off the solvent completely from the obtained filtrate under reduced pressure. Dichloromethane (330 ml) was added to the reaction mixture and added to a pre-cooled mixture of triethyl phosphonoacetate (227.3 gms), potassium tertiary butoxide (113.8 gms) and dichloromethane at 0-5° C. and stirred for 5 hours at the same temperature. Sodium chloride solution (99 gm dissolved in 330 ml of water) was added to the reaction mixture at 0-5° C. Filtered the reaction mixture through hyflow bed and washed with dichloromethane. Both the organic and aqueous layers were separated and distilled off the solvent completely from the organic layer under reduced pressure.

Tetrahydrofuran (168 ml) was added to the above obtained compound at 25-30° C. and cooled to 0-5° C. Nitromethane (38.3 gms) was added to the reaction mixture at 0-5° C. and stirred for 10 minutes at the same temperature. Tetrabutyl ammoniumfluoride solution (164.5 gm dissolved in 840 ml of tetrahydrofuran) was slowly added to the reaction mixture at 0-5° C. and stirred for 5 hours at the same temperature. Dichloromethane (252 ml) and sodium bicarbonate solution (21 gm dissolved in 420 ml of water) were added to the reaction mixture at 0-5° C. and stirred for 10 minutes at the same temperature. Both the organic and aqueous layers were separated and washed the organic layer with sodium chloride solution and distilled off the solvent completely from organic layer under reduced pressure.

Tetrahydrofuran (840 ml) was added to the reaction mixture at 25-30° C. and slowly added to a mixture of sodium borohydride (36.6 gms), lithium bromide (82.9 gms) and tetrahydrofuran at 25-30° C. Stirred the reaction mixture for 60 minutes at 25-30° C. Heated the reaction mixture to 45-50° C. and stirred for 24 hours at the same temperature. Cooled the reaction mixture to 0-5° C. and ammonium chloride solution (147 gm dissolved in 420 ml of water) was slowly added to the reaction mixture at the same temperature. Filtered the reaction mixture through hyflow bed and washed with tetrahydrofuran. Both the organic and aqueous layers were separated. Potassium tertiarybutoxide (39.2 gms) was added to the organic layer at 25-30° C. and stirred for 20 minutes at the same temperature. Reaction mixture was slowly added to pre-cooled aqueous sulfuric acid solution at 0-5° C. and stirred for 20 minutes at the same temperature. Raised the temperature of the reaction mixture to 25-30° C. and stirred for 5 hours at the same temperature.

Triethylamine (46.46 gms) was added to the reaction mixture at 0-5° C. and stirred for 30 minutes at the same temperature. Filtered the reaction mixture through hyflow bed and washed with tetrahydrofuran. Distilled off the solvent completely from the obtained filtrate under reduced pressure. Ethylacetate (320 ml) was added to the reaction mixture at 25-30° C. Filtered the reaction mixture through hyflow bed and washed with ethyl acetate. Distilled off the solvent completely from the obtained filtrate under reduced pressure. Ethylacetate (64 ml) was again added to the reaction mixture at 25-30° C. and distilled off the solvent completely from the reaction mixture under reduced pressure.

Yield: 22 gms.

Example-17: Preparation of 2,5-dioxopyrrolidin-1-yl-((3R,3aS,6aR)-hexahydrofuro[2,3-b]furan-3-yl) carbonate N,N-disuccinmidyl carbonate (44.28 gms) and pyridine (23.3 ml) were added to a mixture of (3R,3aS,6aR)-hexahydrofuro[2,3-b]furan-3-ol (15 gms) and dichloromethane (150 ml) at 25-30° C. and stirred for 10 minutes at the same temperature. Heated the reaction mixture to 40-45° and stirred for 17 hours at the same temperature. Distilled off the solvent completely from the reaction mixture under reduced pressure. Dichloromethane (150 ml) and water (75 ml) were added to the reaction mixture at 25-30° C. and stirred for 15 minutes at the same temperature. Filtered the reaction mixture through hyflow bed and washed with dichloromethane. Both the organic and aqueous layers were separated from the obtained filtrate. Organic layer was washed with citric acid solution (0.75 gm dissolved in 30 ml of water) then followed by with water. Distilled off the solvent completely from the organic layer under reduced pressure. n-hexane (45 ml) was added to the reaction mixture and distilled off the solvent completely from the reaction mixture, n-hexane (45 ml) was again added to the reaction mixture and distilled off the solvent completely from the reaction mixture.

Pre-cooled methanol (75 ml) was added to the reaction mixture at 0-5° C. and stirred for 45 minutes at the same temperature. Filtered the precipitated solid, washed with methanol and dried to get the title compound. Yield: 25 gms.

Example-18: Preparation of Darunavir

4-Amino-N-((2R,3S)-3-amino-2-hydroxy-4-phenylbutyl)-N-isobutylbenzene sulfonamide (159 gms) was added to a mixture of 2,5-dioxopyrrolidin-1-yl-((3R,3aS,6aR)-hexahydrofuro[2,3-b]furan-3-yl) carbonate (100 gms) and methanol (500 ml) at 25-30° C. Triethylamine (37.2 gms) was slowly added to the reaction mixture at 25-30° C. and stirred for 3 hours at the same temperature. Cooled the reaction mixture to 0-3° C. and stirred for 2 hours at the same temperature. Filtered the precipitated solid, washed with pre-cooled methanol and dried to get the title compound.

Yield: 182 gms.

Example-19: Preparation of Amorphous form of Darunavir

A mixture of Darunavir (80 gms), dichloromethane (53 ml) and methanol (346 ml) were stirred for 10 minutes at 25-30° C. Heated the reaction mixture to 50-55° C. and stirred for 20 minutes at the same temperature. Cooled the reaction mixture to 0-3° C. and stirred for 4 hours at the same temperature. Filtered the precipitated solid and washed with methanol.

Methanol (249 ml) and dichloromethane (38.4 ml) were added to the obtained wet compound at 25-30° C. and stirred for 15 minutes at the same temperature. Heated the reaction mixture to 50-55° C. and stirred for 20 minutes at the same temperature. Carbon (8 gms) was added to the reaction mixture at 50-55° C. and stirred for 30 minutes at the same temperature. Filtered the reaction mixture through hyflow bed and washed with a mixture of methanol and dichloromethane. Cooled the obtained filtrate to 0-3° C. and stirred for 4 hours at the same temperature. Filtered the reaction mixture and washed with methanol.

Methanol (1.6 ml) and dichloromethane (160 ml) were added to the obtained wet compound at 25-30° C. and stirred for 20 minutes at the same temperature. Filtered the reaction mixture through hyflow bed and washed with dichloromethane. Distilled off the solvent completely from the reaction mixture under reduced pressure. Cyclohexane (160 ml) was added to the obtained solid at 25-30° C. and stirred for 4 hours at the same temperature. Filtered the precipitated solid, washed with cyclohexane and dried to get the title compound.

Yield: 65 gms.

We claim:

1. A process for the preparation of (3R,3aS,6aR)-hexahydrofuro[2,3-b]furan-3-ol compound of formula-2, Formula-2

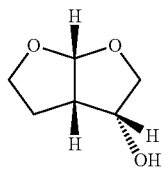

comprising cyclization of (R)-3-((R)-2,2-dimethyl-1,3-dioxolan-4-yl)-4-nitrobutan-1-ol compound of formula-10, Formula-10

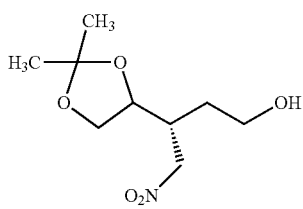

in presence of a base and an inorganic acid in a solvent to obtain the compound of formula-2;

wherein the solvent is not an alcohol.

2. The process according to claim 1, wherein the solvent is selected from the group consisting of ester solvents, ether solvents, chloro solvents, hydrocarbon solvents, ketone solvents, polar solvents, and a mixture thereof.

3. The process according to claim 1, wherein the base is potassium tert-butoxide, the inorganic acid is aqueous sulfuric acid, and the solvent is tetrahydrofuran.

4. A process for the preparation of formula-2, comprising:

a) reduction of (R)-ethyl 3-((R)-2,2-dimethyl-1,3-dioxolan-4-yl)-4-nitrobutanoate compound of formula-9, Formula-9

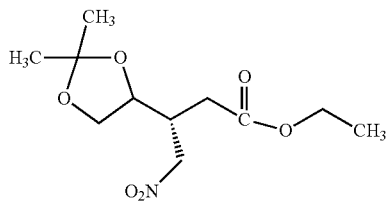

with a reducing agent in presence of lithium bromide in a solvent to obtain compound of formula-10, b) cyclization of the compound of formula-10 in presence of a base and an inorganic acid in a solvent to obtain (3R,3aS,6aR)-hexahydrofuro[2,3-b] furan-3-ol compound of formula-2; wherein the solvent is not an alcohol.

5. A process for the preparation of compound of formula-2, comprising cyclization of a compound of formula-10 in presence of potassium tert-butoxide and aqueous sulfuric acid in tetrahydrofuran to obtain compound of formula-2.

6. The process according to claim 1, further comprising:

a) reacting the compound of formula-2 with N,N'-disuccinimidyl carbonate compound of formula-13

Formula 13

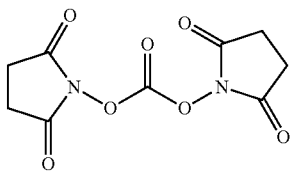

in presence of pyridine in dichloromethane to obtain 2,5-dioxopyrrolidin-1-yl(3R,3aS,6aR)-hexahydrofuro[2,3-b]furan-3-yl carbonate compound of formula-14, Formula 14

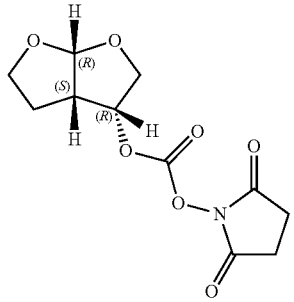

b) optionally purifying the compound obtained in step-a) using n-hexane and methanol, c) reacting compound obtained in step-a) or step-b) with 4-amino-N-((2R,3S)-3-amino-2-hydroxy-4-phenylbutyl)-N-isobutylbenzenesulfonamide compound of formula-15

Formula 15

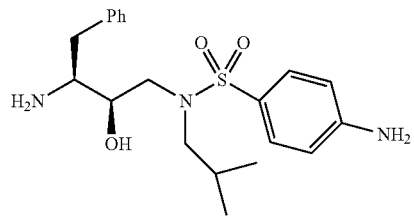

in presence of triethylamine in methanol to obtain [(1S,2R)-3-[[(4-aminophenyl)sulfonyl](2-methyl propyl)amino]-2-hydroxy-1-(phenylmethyl)propyl] carbamic acid (3R,3aS,6aR)-hexahydrofuro[2,3-b]furan-3-yl ester compound of formula-1, Formula-1

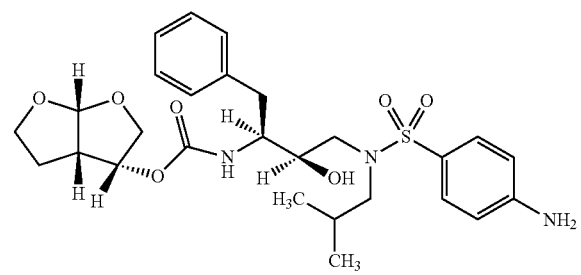

d) optionally purifying the compound of formula-1 obtained in step-c) in a mixture of dichloromethane and methanol and followed by slurrying the obtained compound in cyclohexane to obtain pure amorphous compound of formula-1.

7. The process according to claim 1, further comprising converting compound of formula-2 to compound of formula-1.

8. The process according to claim 4, wherein the solvent is selected from the group consisting of ester solvents, ether solvents, chloro solvents, hydrocarbon solvents, ketone solvents, polar solvents, and a mixture thereof.

9. The process according to claim 4, wherein the base is selected from an organic or an inorganic base.

10. The process according to claim 4, wherein the reducing agent is selected from the group consisting of Lithium aluminum hydride (LiAlH$_4$), hydroquinone, sodium amalgum, diborane, sodium borohydride, lithium borohydride, compounds containing the Sn$^{+2}$ ion such as tin(II)chloride, sulfite compounds, hydrazine, zinc-mercury amalgum, diisobutylaluminum hydride (DIBAL-H), Lindlar catalyst, dithiothretol (DTT), compounds containing Fe$^{+2}$ ion such as iron(II)sulfate, and carbon monoxide.

11. The process according to claim 4, wherein the inorganic acid is selected from the group consisting of hydrochloric acid, hydrobromic acid, sulfuric acid, nitric acid, phosphoric acid, and sulfamic acid.

12. The process according to claim 1, wherein the base is selected from an organic or an inorganic base.

13. The process according to claim 1, wherein the inorganic acid is selected from the group consisting of hydrochloric acid, hydrobromic acid, sulfuric acid, nitric acid, phosphoric acid, and sulfamic acid.

14. The process according to claim 1 further comprising a process for preparation of compound of formula-10, wherein the process for preparation of compound of formula-10 comprises one or more of the following steps:

a) reacting L-Ascorbic acid compound of formula-3

Formula 3

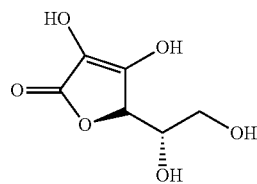

Ia-3 with 2,2-dimethoxypropane in a solvent to obtain 5,6-O-isopropylidene-L-ascorbic acid compound of formula-4,

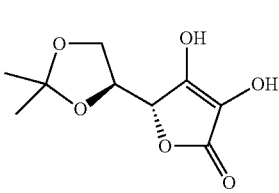

Formula-4 b) oxidizing compound of formula-4 with an oxidizing agent in presence of sodium hydroxide in a solvent to obtain sodium salt of 3,4-O-isopropylidene-L-threonic acid compound of formula-16,

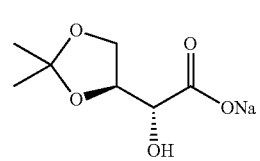

Formula-16 c) reacting compound of formula-16 with an alkylating agent in presence of a base in a solvent to obtain (R)-methyl-2-((S)-2,2-dimethyl-1,3-dioxolan-4-yl)-2-hydroxyacetate compound of formula-17,

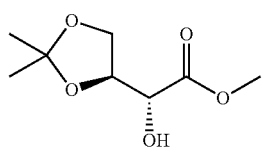

Formula-17 d) reduction of compound of formula-17 with a reducing agent in a solvent to obtain (S)-1-((S)-2,2-dimethyl-1,3-dioxolan-4-yl)ethane-1,2-diol compound of formula-18,

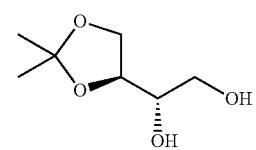

Formula-18 e) reacting compound of formula-18 with sodium periodate in presence of base in a solvent to obtain (S)-2,2-dimethyl-1,3-dioxolane-4-carbaldehyde compound of formula-6,

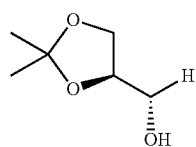

Formula-6 f) reacting compound of formula-6 with ethyl-2-(diethoxyphosphoryl)acetate compound of formula-7

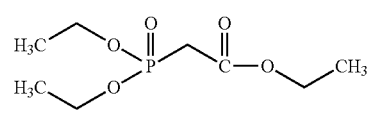

Formula-7 in presence of a base in a solvent to obtain α,β-unsaturated ester i.e., (R,E)-ethyl 3-(2,2-dimethyl-1,3-dioxolan-4-yl)acrylate compound of formula-8,

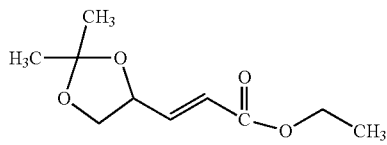

Formula-8 g) reacting ester compound of formula-8 with nitromethane in presence of a base in a solvent to obtain (R)-ethyl 3-((R)-2,2-dimethyl-1,3-dioxolan-4-yl)-4-nitrobutanoate compound of formula-9, Formula-9

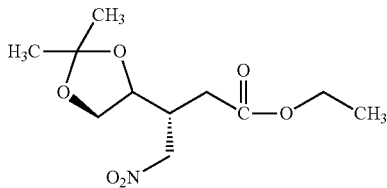

h) reduction of compound of formula-9 with a reducing agent in presence of lithium bromide in a solvent to obtain the compound of formula-10.

15. The process of claim 14, wherein the one or more steps is carried out in-situ.

16. The process according to claim 14, wherein
the solvent in steps-a) to g) is selected from the group consisting of ester solvents, ether solvents, chloro solvents, hydrocarbon solvents, ketone solvents, alcohol solvents, polar solvents, and a mixture thereof;
the solvent in step-h) is selected from the group consisting of ester solvents, ether solvents, chloro solvents, hydrocarbon solvents, ketone solvents, polar solvents, and a mixture thereof;
the base in steps-c), e), f) and g) is selected from an organic or an inorganic base;
the reducing agent in steps-d) and h) is selected from the group consisting of Lithium aluminum hydride (LiAlH$_4$), hydroquinone, sodium amalgum, diborane, sodium borohydride, lithium borohydride, compounds containing the Sn$^{+2}$ ion such as tin(II)chloride, sulfite compounds, hydrazine, zinc-mercury amalgum, diisobutylaluminum hydride (DIBAL-H), Lindlar catalyst, dithiothretol (DTT), compounds containing Fe$^{+2}$ ion such as iron(II)sulfate, and carbon monoxide.

17. The process of claim 1, further comprising one or more of the following steps:
a) reacting L-Ascorbic acid compound of formula-3 with 2,2-dimethoxypropane in a solvent to obtain compound of formula-4,
b) oxidizing compound of formula-4 with an oxidizing agent in presence of calcium carbonate in a solvent to obtain calcium salt of 3,4-O-isopropylidene-L-threonic acid compound of formula-5,

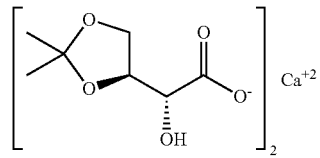

Formula-5 c) reacting compound of formula-5 with sodium hypochloride in presence of acetic acid and sodium acetate in a solvent to obtain compound of formula-6,
d) reacting compound of formula-6 with compound of formula-7 in presence of a base in a solvent to obtain compound of formula-8,
e) reacting compound of formula-8 with nitromethane in presence of a base in a solvent to obtain compound of formula-9, and
f) reduction of compound of formula-9 with a reducing agent in presence of lithium bromide in a solvent to obtain compound of formula-10.

18. The process according to claim 17, wherein
the solvent in step-c), d), e) and f) is selected from the group consisting of ester solvents, ether solvents, chloro solvents, hydrocarbon solvents, ketone solvents, alcohol solvents, polar solvents, and a mixture thereof;
the base in step-d) and e) is selected from an organic or an inorganic base;
the reducing agent in step-f) is selected from the group consisting of Lithium aluminum hydride (LiAlH$_4$), hydroquinone, sodium amalgum, diborane, sodium borohydride, lithium borohydride, compounds containing the Sn$^{+2}$ ion such as tin(II)chloride, sulfite compounds, hydrazine, zinc-mercury amalgum, diisobutylaluminum hydride (DIBAL-H), Lindlar catalyst, dithiothretol (DTT), compounds containing Fe$^{+2}$ ion such as iron(II)sulfate, and carbon monoxide.

* * * * *